(12) United States Patent
Tucker et al.

(10) Patent No.: US 10,194,824 B1
(45) Date of Patent: Feb. 5, 2019

(54) METHOD FOR USING ELECTRICAL STIMULATION FOR CEREBRAL NETWORK ANALYSIS

(71) Applicant: PHILIPS NORTH AMERICA LLC, Andover, MA (US)

(72) Inventors: Don M. Tucker, Eugene, OR (US); Erik Anderson, Eugene, OR (US); Phan Luu, Eugene, OR (US)

(73) Assignee: PHILIPS NORTH AMERICA LLC, Andover, MA (US)

(*) Notice: Subject to any disclaimer, the term of this patent is extended or adjusted under 35 U.S.C. 154(b) by 560 days.

(21) Appl. No.: 14/195,593

(22) Filed: Mar. 3, 2014

(51) Int. Cl.
*A61B 5/04* (2006.01)
*A61B 5/0484* (2006.01)

(52) U.S. Cl.
CPC ........ *A61B 5/0484* (2013.01); *A61B 5/04012* (2013.01)

(58) Field of Classification Search
CPC combination set(s) only.
See application file for complete search history.

(56) References Cited

U.S. PATENT DOCUMENTS

| | | | |
|---|---|---|---|
| 6,594,521 | B2 | 7/2003 | Tucker |
| 6,907,280 | B2 | 6/2005 | Becerra et al. |
| 7,809,434 | B2 | 10/2010 | Kofol et al. |
| 7,840,039 | B2 | 11/2010 | Fuchs |
| 2006/0149160 | A1 | 7/2006 | Kofol et al. |
| 2009/0306532 | A1* | 12/2009 | Tucker ............ A61B 5/0476 600/544 |
| 2012/0157817 | A1* | 6/2012 | Tucker ............ A61B 5/0476 600/383 |
| 2015/0134031 | A1* | 5/2015 | Moffitt ............ A61N 1/37264 607/62 |

OTHER PUBLICATIONS

European Search Report, dated Jun. 25, 2012, Electrical Geodesics, Inc, 8 Pages.
European Office Action, dated Apr. 12, 2010, Electrical Geodesics, Inc, 1 Page.
Article 94(3) EPC Communi, dated May 9, 2014, Electrical Geodesics, Inc, 33 Pages.
Article 94(3) EPC Communi, dated May 9, 2014, Electrical Geodesics, Inc, 32 Pages.
Article 94(3) EPC Communi, dated Nov. 10, 2014, Electrical Geodesics, Inc, 6 Pages.
Article 94(3) EPC Communi, dated Nov. 10, 2014, Electrical Geodesics, Inc, 8 Pages.

* cited by examiner

*Primary Examiner* — Navin Natnithithadha
*Assistant Examiner* — Eric Messersmith
(74) *Attorney, Agent, or Firm* — Sherry Womack Austin (57) ABSTRACT

A method for using electrical stimulation for cerebral network analysis. A first source localization procedure is performed, including a first source measurement procedure which produces first source measurement data, using the first source measurement data to find a solution to a first ill-posed problem which provides a first estimated location of the source. The body is electrically stimulated by targeting the first estimated location, and a second, fast source measurement procedure producing second source measurement data is performed thereafter while measurable effects of the step of stimulating, on the source, still remain. The second source measurement data are compared with the first source measurement data for assessing an extent to which the first estimated location is correct.

44 Claims, 4 Drawing Sheets

METHOD FOR USING ELECTRICAL STIMULATION FOR CEREBRAL NETWORK ANALYSIS

FIELD OF THE INVENTION

The present invention relates to the fields of electrical brain stimulation, brain source localization, and tractography.

BACKGROUND

Sources of electrical brain activity are localized groups or "patches" of neurons that have their electrical polarizations aligned and "oscillating," or periodically reversing direction, substantially in unison. This electrical activity is propagated away from the sources, by conduction to other patches of neurons through a network of "tracts," and by radiation through the various head tissues, namely brain, skull, and skin; and within the brain, gray matter, white matter, and cerebrospinal fluid. The conductive aspect of this electrical activity is responsible for physiological effects in the brain and/or elsewhere in the body.

It is important for understanding how source activity produces an effect, and for electrically stimulating the sources to cause that effect, to know where the sources are. The process of determining this is called "source localization." It is typically carried out by electroencephalography (EEG), though other non-invasive techniques, such as magnetoencelephography (MEG), and functional magnetic resonance imaging (fMRI), are also used.

EEG is performed by placing electrodes on the surface of the head and measuring the surface potentials (voltages) that result from the radiative aspect of the source activity. These data are used to solve a mathematically "ill-posed" problem, known in the art as the "inverse problem." The inverse problem is to infer from the surface fields a hypothetical source activity that is consistent with producing those fields.

Specifying the inverse problem requires formulating an anatomical model of the head defining the locations and extent of the different head tissues. Each of these tissue types has a known characteristic impedance, so the anatomical model allows for calculating impedances of the various paths that electromagnetic radiation from a source can take as it radiates through the head tissues, ultimately to be received at the head surface electrodes.

The anatomical head model may be obtained by use of standard (non-functional) MRI of a particular subject's brain, or it may be hypothesized as a generalized model. In either case, the inverse problem suffers generally from being insufficiently constrained for unambiguous solution.

Model sources, preferably dipolar current sources, are virtually disposed within the anatomical model at corresponding patches, and the positions and/or strengths of the sources are iteratively manipulated until a satisfactory agreement is reached between calculated values of surface potential and those that are actually measured.

A significant innovation in the field of EEG source localization is described in U.S. Pat. No. 6,330,470, according to which injected currents are used in combination with measured surface potentials are used for more precisely characterizing the internal impedances by taking advantage of reciprocity between measured surface potentials and injected currents.

Another significant innovation in the field of EEG source localization is described in U.S. patent application Publication No. 2009/0306532, incorporated by reference herein in its entirety, according to which a tractographic analysis is used as a constraint on the solutions to the inverse problem.

Further, the '532 publication introduced the idea that, just like tractography can be used as an aid in source localization, source localization can be used as an aid in tractography.

It is often useful for research or therapeutic purposes to cause the brain to produce a desired effect. This is accomplished by electrically stimulating the same sources that were recognized from a source localization procedure to produce that effect, by injecting currents through head-surface electrodes as required to target those sources. In such cases it is often desirable to use EEG as the source localization procedure because the same apparatus is easily adapted for applying electrical stimulation. Moreover, using the same electrodes for source localization and electrical stimulation allows for taking advantage of reciprocity between measured surface potentials and injected currents in the manner taught in U.S. Pat. No. 6,594,521, to improve the precision of the stimulation.

Summarizing, a patch of neurons defining a source may be more precisely located by use of methods such as described in the '470 patent and the '532 publication, and may be more precisely targeted for stimulation by application of methods such as those described in the '521 patent. It is an object of the present invention to combine these methodologies to further improve the precision of brain source localization.

SUMMARY

Disclosed are methods for using electrical stimulation for cerebral network analysis. In a basic method according to the invention, a first source localization procedure is performed, which includes a first source measurement procedure which produces first source measurement data. The first source localization procedure uses the first source measurement data to find a solution to a first ill-posed problem which provides a first estimated location of the source. The method then includes electrically stimulating the body by targeting the first estimated location. After ceasing the step of stimulating, the method further includes performing a second, fast source measurement procedure while measurable effects of the step of stimulating, on the source, still remain. The second source measurement procedure produces second source measurement data that are compared with the first source measurement data for assessing an extent to which the first estimated location is correct.

The method may also include performing a tractographic analysis taking account of the first estimated location.

Where the comparison indicates that the first estimated location is incorrect, the method includes performing a second source localization procedure using the second source measurement data in combination with information obtained from the first source localization procedure to provide a revised estimated location of the source.

The second source localization procedure may include using a combination of the first and second source measurement data to find a solution to a second ill-posed problem to provide the revised estimated location of the source.

In addition or in the alternative, the second source localization procedure may include using the second measurement data to find a solution to a second ill-posed problem which provides a second estimated location of the source, wherein the revised estimated location is based, at least in part, on a combination of the first and second estimated.

Also where the comparison indicates that the first estimated location is incorrect, the method may also include performing a revised tractographic analysis taking the revised estimated location into account.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

Figure 1:
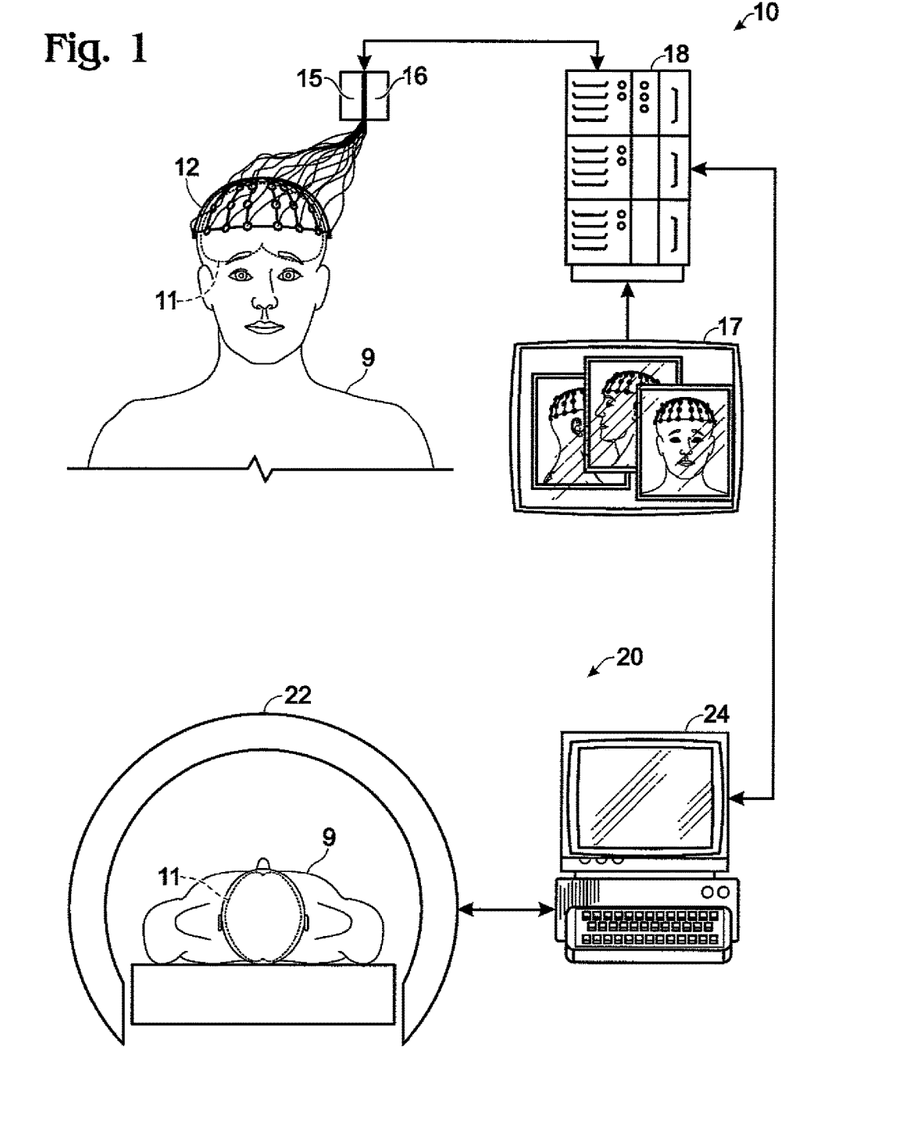
FIG. 1 is a block diagram of a system for using electrical stimulation for cerebral network analysis according to the invention.

FIG. 1 shows a system 10 for using electrical stimulation for cerebral network analysis according to the present invention is shown. The term "cerebral network" refers to networks of neurons in the brain, and more particularly in the cortex, which can be modeled as "sources" of electrical activity (gray matter) that are electrically connected to one another through a network of "tracts" (white matter). The system 10 is adapted for analyzing and stimulating a typical cerebral network, that in the brain 11 of a living human subject 9; however, it will be understood that the principles of the invention could be usefully applied to analyzing or stimulating any network of electrical activity by external means.

As noted previously, the '532 publication shows that tractography can be used as an aid in EEG source localization procedure, and an EEG source localization procedure can be used as an aid in tractography. Here it will be understood more generally that tractographic and source localization procedures are complements. Hence the term "cerebral network analysis" will be understood as generic for both.

The typical source localization procedure is by EEG, and the invention will be described using that example. However, it will be understood that, as noted previously, other source localization procedures can be employed, in which case persons of ordinary skill will know the modifications that would need to be made to the system 10.

It should also be understood that an EEG source localization procedure has two steps, a first step of acquiring source measurement data, and a second step of using the source measurement data for finding a solution to the inverse problem which provides an estimated location of the sources. The first step, referred to herein as a "source measurement procedure," is distinct from the second step, referred to herein as a "localization problem solving procedure," and may be useful apart from it, and therefore apart from a full source localization procedure.

For both source measurement procedures and electrical stimulation the system 10 provides a large number (e.g., 256) of electrodes 12 that are placed on the surface of a subject's head so as to make electrical contact with the skin. The electrodes are electrically conductive, typically being formed of a pure metal such as copper. Each electrode, relative to each other electrode, defines an electrical "port."

As is well known in the art, it is important to know the locations of the electrodes. A preferred methodology for determining this utilizes a photogrammetric system 17 as described in U.S. Pat. No. 7,190,826.

For source measurement procedures, the system 10 measures surface potential (voltage) differences across the ports caused by brain source activity. The electrodes 12 are connected to a multi-channel volt-meter 15 for measuring the potentials, each channel corresponding to a port. Data from the volt-meter 15 and the photogrammetric system 17 are input to a computer 18. The computer utilizes these data as the measured results for comparison with the results predicted by the model sources, for solving the inverse problem.

For source localization procedures, the computer 18 may be used to output control signals for controlling a multi-channel current source 16, each channel corresponding to a port. The current source drives currents into the ports, into the head and ultimately into the brain. Relatively low levels of this "current injection" may be used for characterizing the internal impedance paths within the brain as needed for solving the inverse problem as described in the '470 patent.

For both source localization and tractographic procedures, the system 10 includes an MRI sub-system 20, for specifying the anatomical head model and for performing the tractographic procedure on the same subject 9.

The MRI sub-system 20 includes a scanner 22, and a computer 24 for controlling the scanner, for receiving tomographic data indicating successive cross-sections of the subject's brain, and for producing a standard three-dimensional "standard" image of the brain which is used for the anatomical head model. The computer 24 may be the same computer or network of computers as the computer 18.

For tractographic procedures, the MRI sub-system 20 is used for producing a "diffusion tensor" image of the brain showing, in particular, selected neural tracts along with a computer calculated probabilistic assessment of the connectivity of those tracts.

By comparing the standard image to the diffusion tensor image, the model sources can be physically associated with tracts, and thus the probabilistic assessment of tract connectivity—the tractographic analysis—provides a corresponding assessment of source connectivity. In turn, the assessment of source connectivity provides an indication of whether the sources should co-vary, i.e., whether activity at one source should correlate with activity at another. In addition, the diffusion tensor image shows the lengths of the tracts, and this indicates how the sources should co-vary, i.e., how activity at one source should be related to activity at another source in amplitude and/or time.

The tractographic analysis is an ill-posed problem like the inverse problem. Moreover, as described in the '532 application the result of an EEG source localization is useful to constrain a tractographic analysis, and the result of a tractographic analysis is useful to constrain an EEG source localization.

Here it will be understood more generally that the result of a source localization is useful to inform a tractography, and the result of a tractography is useful to inform a source localization. For best results in solving either problem it is preferable to solve them both together, in a series of circular iterations whereby a tentative solution to a first of these problems is used as a constraint on a tentative solution to the other, and the tentative solution to the latter is used as a constraint on the next tentative solution to the former, the process settling to completion when the tentative solutions to both problems converge, or stop changing.

For stimulation, higher levels of current injection than those used in source localization are employed for stimulating quiescent sources to be active. More particularly, the object is to stimulate sources that are not active at present but that were localized by virtue of their prior activity.

It is routine practice to use source localization information to target the same sources for stimulation; so it is known how to inject currents so as to target a source that is estimated to be present at a particular location. But it is a novel feature of the present invention to use results of a stimulation to go back and improve a source localization, or a tractography, i.e., to improve a cerebral network analysis.

The present invention recognizes that the stimulation that follows a source localization can be used as a test of a hypothesis that the source localization is correct; and if it is not correct, can be used to improve it. Both features of testing and improving can be achieved according to the invention by establishing a feedback loop between stimulation and source localization, observing an effect (a) of the stimulation, comparing it to a corresponding or related effect (b) predicted by the source localization, and, if there is a significant difference between (a) and (b), performing a second source localization taking the difference into account in an effort to minimize it.

Likewise, the present invention recognizes that the results of a stimulation can be used to test the validity of a tractographic analysis; and if it is not valid, can be used to improve it. The same feedback can be used for both purposes; observing the difference between an effect (a) of the stimulation, comparing it to a corresponding or related result (b) of the tractographic analysis, and, if there is a significant difference between (a) and (b), modifying the tractographic analysis taking the difference into account in an effort to minimize it.

The effect of stimulation may in some cases be capable of direct observation. But it is generally necessary, for gauging a subject's response to an electrical brain stimulation to a desired degree of precision, to follow the stimulation with another source measurement procedure that can measure source activity within the short time after the stimulus has been removed but before the stimulated activity has decayed. For purposes herein, a source measurement procedure will be considered sufficiently "fast" for this purpose if it is capable of sensing and recording source activity having a duration of 100 ms or less. As examples, EEG and MEG are fast source measurement procedures, whereas fMRI is not.

As one example of using electrical stimulation for cerebral network analysis according to the invention, a subject is shown an image. At the same time an EEG source measurement procedure is performed on the subject whereby the subject's brain source activity resulting from that visual stimulus is monitored, resulting in first, encephalographic, source measurement data.

The system 10 is also used to inject currents into the subject's brain using the same electrodes that were used for obtaining the first source measurement data, for characterizing internal impedances as described in the '470 patent.

The subject is also scanned using the MRI sub-system 20 of the system 10, to obtain a standard MRI image for constructing a head model for the subject.

In a first source localization problem solving procedure, the head model, impedance characterizations, and first source measurement data are used to specify a first inverse problem, which when solved provides first estimated locations for the sources that were active in response to the visual stimulus.

The MRI sub-system 20 is also used to perform a first tractographic analysis that is directed to (or "seeded" at) the first estimated locations for the sources, whereby a diffusion tensor image of the tracts near those locations is used to obtain a probabilistic assessment of the connectivity of the sources at those locations. The probabilistic assessment of source connectivity is useful as a constraint on the first localization problem solving procedure.

Next, a stimulation is devised in a standard manner based on the first estimated source locations to target the same source or sources. The stimulation is applied and then stopped at time t=0. The activity of the sources which were stimulated decays, roughly, exponentially with a time constant of, say, 5 ms. Accordingly, a second source measurement procedure is conducted between t=0 and 5 ms to measure the residual source activity caused by the stimulation, defining second source measurement data. The second source measurement data can be compared directly to the first source measurement data to determine the extent to which they agree. If to an acceptable tolerance they do agree, the first estimated source locations can be considered to be correct and no further steps are required.

On the other hand, if the differences between the first and second source measurement data fall outside the acceptable tolerance, the stimulation is recognized to have confirmed that there was an error in the first source localization. Then and further, the first and second source measurement data are used together for minimizing the error. More particularly, a second source localization problem solving procedure is performed using a combination of the second source measurement data and information obtained from the first source localization procedure.

The second source localization problem is solved using the second source measurement data in combination with the first source measurement data, such as by using the averages of the first and second measurement data at each of the electrodes.

Alternatively, the second localization problem may be solved using only the second measurement data, resulting in second estimated locations of the sources. Then, one example of revising the first estimated locations of the sources taking the results of the stimulation into account is to average the corresponding first and second estimated locations.

The results of a stimulation can also be used to revise a tractographic analysis. Obtaining a probabilistic assessment of tract connectivity is an ill-posed problem the solution to which can be improved by taking account of additional, relevant information. It was already noted that the first estimated source locations were in the example here obtained by taking the first tractographic analysis into account. So there is a forced consistency between the first estimated source locations and the first tractographic analysis. And so to the extent there is disagreement in the first and second source measurement data, there should likewise be disagreement between the first tractographic analysis and that which would have been obtained if the second estimated source locations were taken into account instead of the first estimated source locations. In that case, an improved, revised tractographic analysis can be obtained by taking the improved, revised estimated source locations into account. For example, the problem of finding a most probable tract connectivity can be constrained by assuming the source locations are defined by combining the first and second estimated source locations, such as by averaging them.

Figure 2:
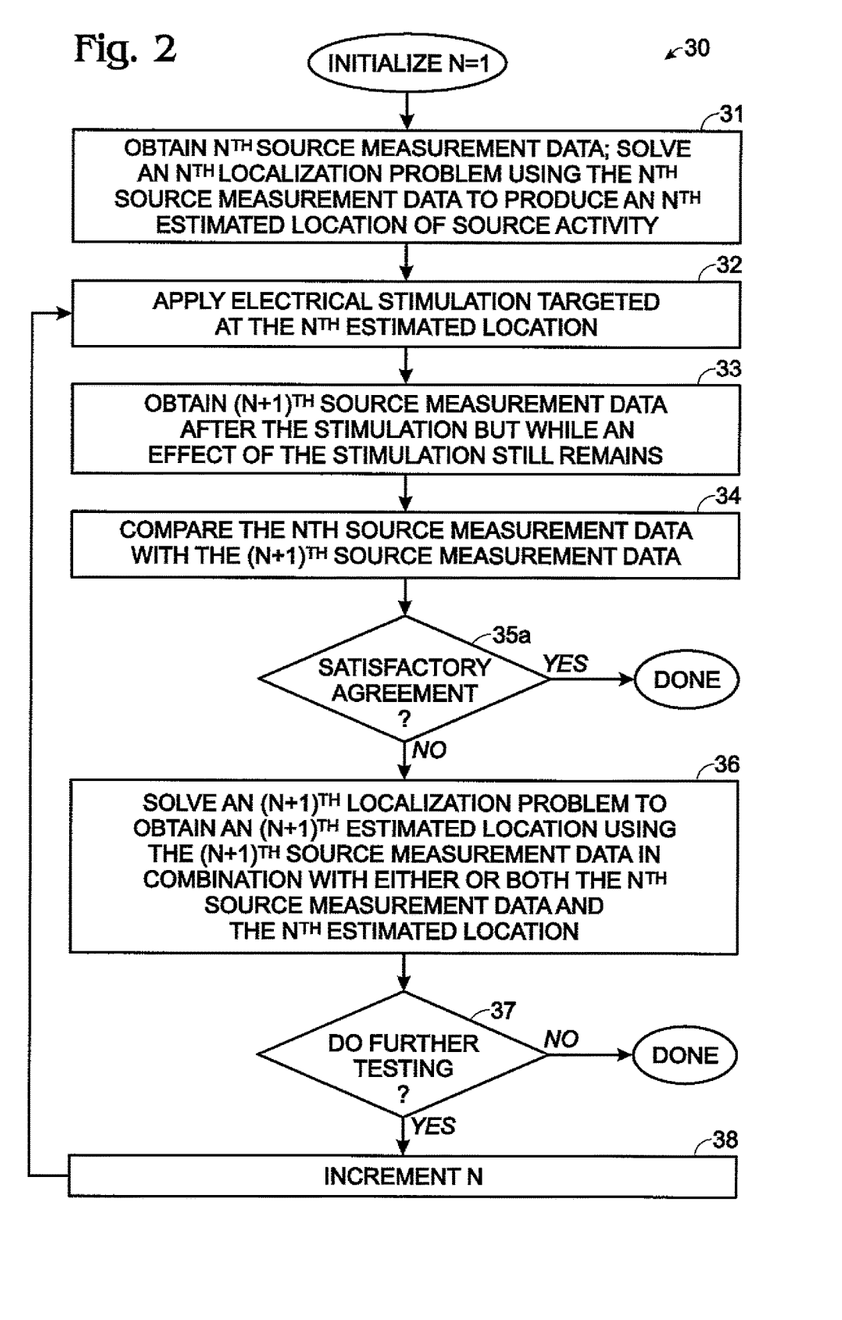
FIG. 2 is a flow chart of a method for using electrical stimulation for source localization according to the invention.
Figure 3A:
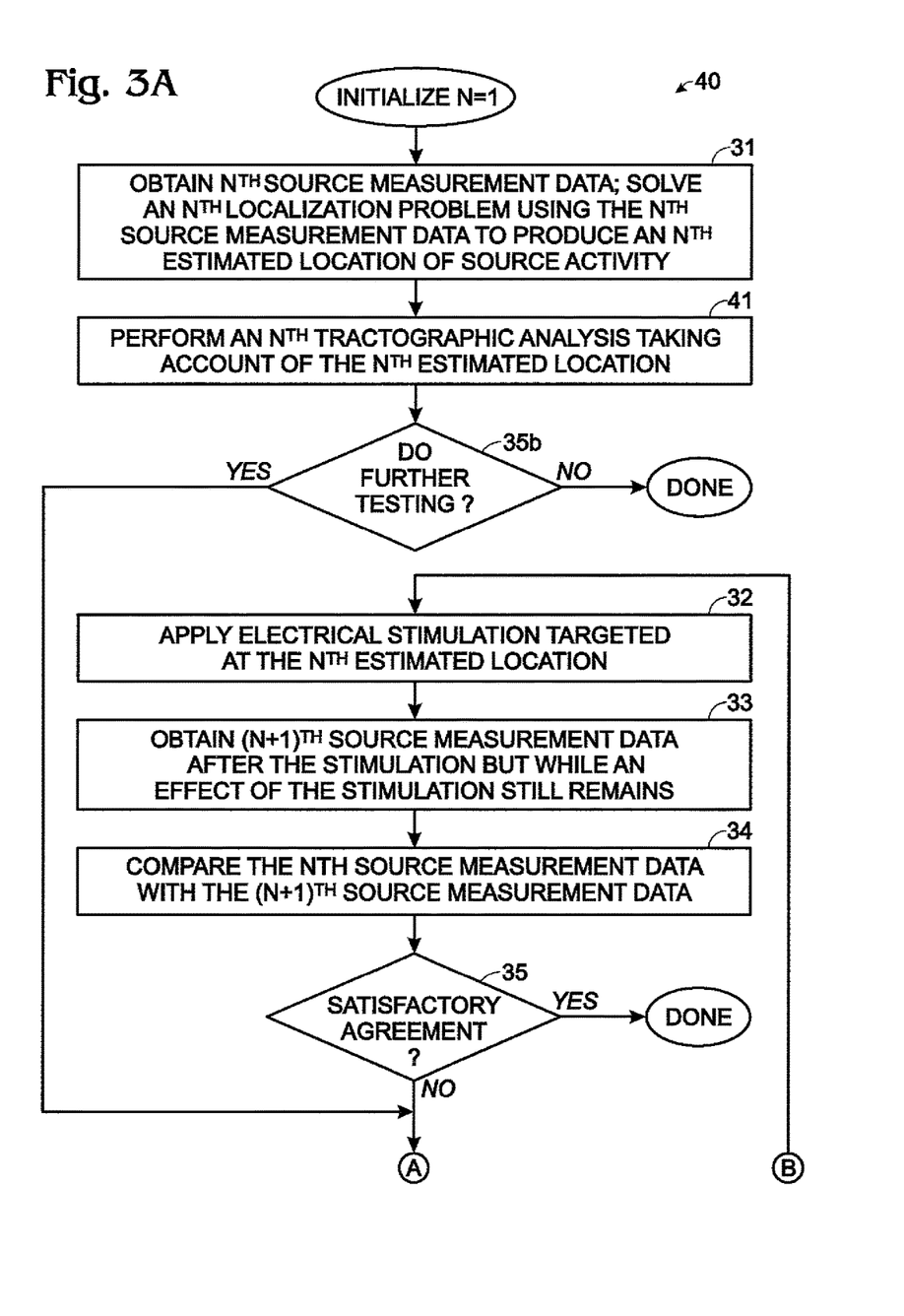
FIGS. 3A and 3B are a flow chart of the method of FIG. 2 extended to using electrical stimulation for tractography according to the invention.
Figure 3B:
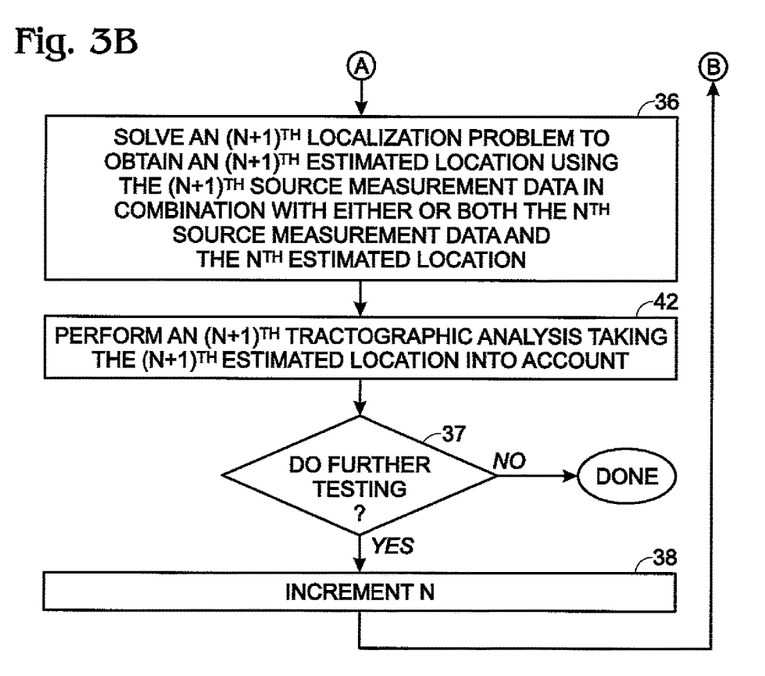

Methods according to the present invention provide for iterating until the solutions to two (or more) parallel problem solving tracks converge. FIGS. 2 and 3 are flow charts that illustrate these iterative capabilities.

FIG. 2 is particularly a flow chart of a basic method 30 according to the invention for using electrical stimulation for source localization. The method 30 begins with a step 31 of obtaining an $N^{th}$ (initially N=1, or "first") source measurement data such as by use of EEG, and solving an $N^{th}$ (initially N=1, or "first") source localization problem using the $N^{th}$ source measurement data.

Next, in step 32, the subject's head is electrically stimulated by targeting the $N^{th}$ estimated locations of the sources.

Next, in step 33, after the electrical stimulation in step 32 is ceased, $(N+1)^{th}$ (initially N+1=2, or "second") source measurement data are obtained by a fast measurement procedure such as another EEG while the sources that were stimulated in step 32 remain active as a result of the stimulation.

Next, in step 34, the $(N+1)^{th}$ measurement data are compared to the $N^{th}$ measurement data to determine the extent to which they agree. If the extent to which the two sets of measurement data agree falls within a satisfactory range of tolerance, the source localization can be deemed to have been successful and the method may be terminated.

Otherwise, the source location established in step 30 can be improved by taking a next step 36 of solving an $(N+1)^{th}$ source localization problem using the $(N+1)^{th}$ source measurement data in combination with either or both the $N^{th}$ source measurement data, and the $N^{th}$ estimated location. The resulting $(N+1)^{th}$ estimated location of the source activity should be more accurate than the $N^{th}$ estimated location, especially where further iterations of the method are performed by proceeding to step 38 (incrementing N) and returning to step 32.

FIGS. 3A and 3B are a flow chart of a basic method 40 according to the invention for using electrical stimulation for tractography. The method 40 utilizes results of the method 30 of FIG. 2. During or following step 32 of the method 30, shown in both FIGS. 2 and 3A, an $N^{th}$ (initially N=1, or "first") tractography is performed at step 41. The $N^{th}$ tractography is performed taking the $N^{th}$ estimated location of source activity from step 32 into account. If the result of step 35a (FIG. 2) of method 30 is that there was satisfactory agreement between the $N^{th}$ source measurement data and the $(N+1)^{th}$ source measurement data, the $N^{th}$ tractography can be deemed to be successful at 35b (FIG. 3A) and the method may again be terminated. Otherwise, the method 40 continues with step 36 (shown in both FIGS. 2 and 3B) of the method 30.

During or following step 36 of the method 30, the method 40 may be continued to obtain an improved tractography at step 42 (FIG. 3B). The resulting $(N+1)^{th}$ tractography should be more accurate than the $N^{th}$ tractography, especially where further iterations of the method are performed by proceeding to step 38 (FIGS. 2 and 3B) of the method 30 (incrementing N) and returning to step 32 (FIGS. 2 and 3A).

Electrical brain stimulation may be used as a probe according to the invention for cerebral network analysis of any type that involves solving problems that are ambiguous or indefinite, i.e., "ill-posed," and which can therefore become less ambiguous and more definite by the imposition of additional, relevant constraints.

It is to be understood that, while a specific method for using electrical stimulation for cerebral network analysis have been shown and described as preferred, other methods in accordance with the principles described herein could be utilized without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for analyzing a cerebral network including localizing a source of electrical activity in the brain comprising:
    performing a first source localization procedure including a first source measurement procedure which produces first source measurement data, and a first localization problem solving procedure using the first source measurement data to find a solution to a first ill-posed problem which is used to provide a first estimated location of the source;
    electrically stimulating the brain by targeting the first estimated location;
    ceasing the step of stimulating and thereafter performing a second, fast source measurement procedure while measurable effects of the step of stimulating, on the source, still remain, the second source measurement procedure producing second source measurement data; and
    comparing the second source measurement data with the first source measurement data for assessing an extent to which the first estimated location is correct.

2. The method of claim 1 further comprising performing a tractographic analysis, including obtaining a first probabilistic estimate of tract connectivity taking account of the first estimated location.

3. The method of claim 1, where said step of comparing indicates that the first estimated location is not correct, the method further comprising performing a second source localization problem solving procedure using the second source measurement data in combination with information obtained from the first source localization procedure to provide a revised estimated location of the source.

4. The method of claim 3, wherein the second source localization procedure includes using a combination of the first and second source measurement data to find a solution to a second ill-posed problem to provide the revised estimated location of the source.

5. The method of claim 3, wherein the second source localization procedure includes using the second measurement data to find a solution to a second ill-posed problem which provides a second estimated location of the source, wherein the revised estimated location is based, at least in part, on a combination of the first and second estimated locations.

6. The method of claim 2, where said step of comparing indicates that the first estimated location is not correct, the method further comprising performing a second source localization problem solving procedure using the second source measurement data in combination with information obtained from the first source localization procedure to provide a revised estimated location of the source, and performing a revised tractographic analysis, including obtaining a second probabilistic estimate of tract connectivity taking account of the revised estimated location.

7. The method of claim 6, further comprising electrically stimulating the brain by targeting the revised estimated location.

8. The method of claim 5, further comprising electrically stimulating the brain by targeting the revised estimated location.

9. The method of claim 4, further comprising electrically stimulating the brain by targeting the revised estimated location.

10. The method of claim 3, further comprising electrically stimulating the brain by targeting the revised estimated location.

11. The method of claim 2, further comprising electrically stimulating the brain by targeting the revised estimated location.

12. The method of claim 11, wherein each of the first and second localization procedures includes a respective EEG providing the respective first and second source measurement data.

13. The method of claim 10, wherein each of the first and second localization procedures includes a respective EEG providing the respective first and second source measurement data.

14. The method of claim 9, wherein each of the first and second localization procedures includes a respective EEG providing the respective first and second source measurement data.

15. The method of claim 8, wherein each of the first and second localization procedures includes a respective EEG providing the respective first and second source measurement data.

16. The method of claim 7, wherein each of the first and second localization procedures includes a respective EEG providing the respective first and second source measurement data.

17. The method of claim 6, wherein each of the first and second localization procedures includes a respective EEG providing the respective first and second source measurement data.

18. The method of claim 5, wherein each of the first and second localization procedures includes a respective EEG providing the respective first and second source measurement data.

19. The method of claim 4, wherein each of the first and second localization procedures includes a respective EEG providing the respective first and second source measurement data.

20. The method of claim 3, wherein each of the first and second localization procedures includes a respective EEG providing the respective first and second source measurement data.

21. The method of claim 2, wherein each of the first and second localization procedures includes a respective EEG providing the respective first and second source measurement data.

22. The method of claim 1, wherein the first localization procedure includes an EEG providing the first source measurement data.

23. The method of claim 22, wherein the step of stimulating the brain by targeting the first estimated location employs electrodes disposed on the surface of the head.

24. The method of claim 21, wherein the step of stimulating the brain by targeting the first estimated location employs electrodes disposed on the surface of the head.

25. The method of claim 20, wherein the step of stimulating the brain by targeting the first estimated location employs electrodes disposed on the surface of the head.

26. The method of claim 19, wherein the step of stimulating the brain by targeting the first estimated location employs electrodes disposed on the surface of the head.

27. The method of claim 18, wherein the step of stimulating the brain by targeting the first estimated location employs electrodes disposed on the surface of the head.

28. The method of claim 17, wherein the step of stimulating the brain by targeting the first estimated location employs electrodes disposed on the surface of the head.

29. The method of claim 16, wherein the step of stimulating the brain by targeting the first estimated location employs electrodes disposed on the surface of the head.

30. The method of claim 15, wherein the step of stimulating the brain by targeting the first estimated location employs electrodes disposed on the surface of the head.

31. The method of claim 14, wherein the step of stimulating the brain by targeting the first estimated location employs electrodes disposed on the surface of the head.

32. The method of claim 13, wherein the step of stimulating the brain by targeting the first estimated location employs electrodes disposed on the surface of the head.

33. The method of claim 12, wherein the step of stimulating the brain by targeting the first estimated location employs electrodes disposed on the surface of the head.

34. The method of claim 11, wherein the steps of stimulating the brain by targeting the first estimated location and stimulating the brain by targeting the revised estimated location employ electrodes disposed on the surface of the head.

35. The method of claim 10, wherein the steps of stimulating the brain by targeting the first estimated location and stimulating the brain by targeting the revised estimated location employ electrodes disposed on the surface of the head.

36. The method of claim 9, wherein the steps of stimulating the brain by targeting the first estimated location and stimulating the brain by targeting the revised estimated location employ electrodes disposed on the surface of the head.

37. The method of claim 8, wherein the steps of stimulating the brain by targeting the first estimated location and stimulating the brain by targeting the revised estimated location employ electrodes disposed on the surface of the head.

38. The method of claim 7, wherein the steps of stimulating the brain by targeting the first estimated location and stimulating the brain by targeting the revised estimated location employ electrodes disposed on the surface of the head.

39. The method of claim 6, wherein the step of stimulating the brain by targeting the first estimated location employs electrodes disposed on the surface of the head.

40. The method of claim 5, wherein the step of stimulating the brain by targeting the first estimated location employs electrodes disposed on the surface of the head.

41. The method of claim 4, wherein the step of stimulating the brain by targeting the first estimated location employs electrodes disposed on the surface of the head.

42. The method of claim 3, wherein the step of stimulating the brain by targeting the first estimated location employs electrodes disposed on the surface of the head.

43. The method of claim 2, wherein the step of stimulating the brain by targeting the first estimated location employs electrodes disposed on the surface of the head.

44. The method of claim 1, wherein the step of stimulating the brain by targeting the first estimated location employs electrodes disposed on the surface of the head.

* * * * *